(12) United States Patent
Jagannathan et al.

(10) Patent No.: US 11,295,872 B2
(45) Date of Patent: Apr. 5, 2022

(54) RADIATION SENSING THERMOPLASTIC COMPOSITE PANELS

(71) Applicant: CARESTREAM HEALTH, INC., Rochester, NM (US)

(72) Inventors: Seshadri Jagannathan, Rochester, NY (US); Charles M. Rankin, Rochester, NY (US); Lawrence D. Folts, Rochester, NY (US); Barbara Ulreich, Rochester, NY (US); Betsy J. Guffey, Rochester, NY (US); Jean-Marc Inglese, Bussy-Saint-Georges (FR)

( * ) Notice: Subject to any disclaimer, the term of this patent is extended or adjusted under 35 U.S.C. 154(b) by 0 days.

(21) Appl. No.: 16/062,471

(22) PCT Filed: Aug. 5, 2016

(86) PCT No.: PCT/US2016/045764
§ 371 (c)(1),
(2) Date: Jun. 14, 2018

(87) PCT Pub. No.: WO2017/105557
PCT Pub. Date: Jun. 22, 2017

(65) Prior Publication Data
US 2018/0374598 A1    Dec. 27, 2018

Related U.S. Application Data

(60) Provisional application No. 62/266,860, filed on Dec. 14, 2015.

(51) Int. Cl.
| | |
|---|---|
| *G21K 4/00* | (2006.01) |
| *A61B 6/00* | (2006.01) |
| *G01T 1/20* | (2006.01) |
| *C09K 11/77* | (2006.01) |
| *B29C 48/00* | (2019.01) |

(Continued)

(52) U.S. Cl.
CPC .......... *G21K 4/00* (2013.01); *A61B 6/42* (2013.01); *A61B 6/4216* (2013.01); *B29C 43/003* (2013.01); *B29C 45/0001* (2013.01); *B29C 48/022* (2019.02); *C09K 11/7728* (2013.01); *G01T 1/2012* (2013.01); *B32B 27/18* (2013.01); *C09K 11/7733* (2013.01); *G21K 2004/06* (2013.01); *G21K 2004/12* (2013.01)

(58) Field of Classification Search
CPC ..... A61B 6/42; A61B 6/4216; B29C 45/0001; B29C 47/0004; B32B 27/18; C09K 11/7728; C09K 11/7733; G01T 1/2012; G21K 4/00; G21K 2004/06; G21K 2004/12
See application file for complete search history.

(56) References Cited

U.S. PATENT DOCUMENTS

| | | | |
|---|---|---|---|
| 2006/0202134 A1* | 9/2006 | Fukui | C09K 11/671 250/484.4 |
| 2014/0291528 A1* | 10/2014 | Jagannathan | G01T 1/2033 250/361 R |

* cited by examiner

*Primary Examiner* — Mark R Gaworecki

(57) ABSTRACT

A storage phosphor panel can include an extruded inorganic storage phosphor layer including a thermoplastic polymer and an inorganic storage phosphor material, where the extruded inorganic storage phosphor panel has an image quality comparable to that of a traditional solvent coated inorganic storage phosphor screen. Further disclosed are certain exemplary method and/or apparatus embodiments that can provide inorganic storage phosphor panels including a selected blue dye that can be recycled while maintaining sufficient image quality characteristics.

5 Claims, 1 Drawing Sheet

(51) Int. Cl.
*B29C 43/00* (2006.01)
*B29C 45/00* (2006.01)
*B32B 27/18* (2006.01)

RADIATION SENSING THERMOPLASTIC COMPOSITE PANELS

FIELD OF THE INVENTION

The invention relates generally to the field of inorganic storage phosphor materials. More specifically, the invention relates to melt extrudable and/or injection moldable and/or hot-melt pressable composites of inorganic storage phosphor materials and thermoplastic and/or thermoset polymers and methods for making and/or using the same.

BACKGROUND OF THE INVENTION

Near the beginning of the $20^{th}$ century, it was recognized that a medically useful anatomical image could be obtained when a film containing a radiation-sensitive silver halide emulsion is exposed to X-radiation (X-rays) passing through the patient. Subsequently, it was recognized that X-ray exposure could be decreased considerably by placing a radiographic phosphor panel adjacent to the film.

A radiographic phosphor panel typically contains a layer of an inorganic phosphor that can absorb X-rays and emit light to expose the film. The inorganic phosphor layer is generally a crystalline material that responds to X-rays in an image-wise fashion. Radiographic phosphor panels can be classified, based on the type of phosphors used, as prompt emission panels and image storage panels.

Image storage panels (also commonly referred to as "storage phosphor panels") typically contain a storage ("stimulable") phosphor capable of absorbing X-rays and storing its energy until subsequently stimulated to emit light in an image-wise fashion as a function of the stored X-ray pattern. A well-known use for storage phosphor panels is in computed or digital radiography. In these applications, the panel is first image-wise exposed to X-rays, which are absorbed by the inorganic phosphor particles, to create a latent image. While the phosphor particles may fluoresce to some degree, most of the absorbed X-rays are stored therein. At some interval after initial X-ray exposure, the storage phosphor panel is subjected to longer wave length radiation, such as visible or infrared light (e.g., stimulating light), resulting in the emission of the energy stored in the phosphor particles as stimulated luminescence (e.g., stimulated light) that is detected and converted into sequential electrical signals which are processed in order to render a visible image on recording materials, such as light-sensitive films or digital display devices (e.g., television or computer monitors). For example, a storage phosphor panel can be image-wise exposed to X-rays and subsequently stimulated by a laser having a red light or infrared beam, resulting in green or blue light emission that is detected and converted to electrical signals which are processed to render a visible image on a computer monitor. The stimulating light may also be other sources other than a laser (such as LED lamps), that would permit stimulation of a larger area of the storage phosphor, and the detection may be done using a two dimensional detector, such as a CCD or a CMOS device. Thereafter, images from storage phosphor panels can be "erased" by exposure to UV radiation, such as from fluorescent lamps.

Thus, storage phosphor panels are typically expected to store as much incident X-rays as possible while emitting stored energy in a negligible amount until after subsequent stimulation; only after being subjected to stimulating light should the stored energy be released. In this way, storage phosphor panels can be repeatedly used to store and transmit radiation images.

However, there exists a need for improved storage phosphor panels. More specifically, there exists a need for melt extruded or injection molded or hot pressed inorganic storage phosphor panel has an image quality that is comparable to the image quality of the traditional solvent coated screen of equivalent x-ray absorbance.

SUMMARY OF THE INVENTION

An aspect of this application is to advance the art of medical, dental and non-destructive imaging systems.

Another aspect of this application is to address in whole or in part, at least the foregoing and other deficiencies in the related art.

It is another aspect of this application to provide in whole or in part, at least the advantages described herein.

In an aspect, there are provided exemplary melt extruded or injection molded or hot pressed inorganic storage phosphor panel embodiments including a melt extruded or injection molded or hot pressed inorganic storage phosphor layer comprising a thermoplastic polymer and an inorganic storage phosphor material, wherein the melt extruded or injection molded or hot pressed inorganic storage phosphor panel has an image quality that is comparable to or better than the image quality of the traditional solvent coated screen of equivalent x-ray absorbance.

In another aspect, there are also disclosed exemplary inorganic storage phosphor detection system embodiments including a melt extruded or injection molded or hot pressed inorganic storage phosphor panel comprising a melt extruded or injection molded or hot pressed inorganic storage phosphor layer comprising a thermoplastic olefin and an inorganic storage phosphor material.

In a further aspect, there are disclosed exemplary method embodiments of making a melt extruded or injection molded or hot pressed inorganic storage phosphor panel including providing thermoplastic polymer comprising at least one thermoplastic polymer and an inorganic storage phosphor material; and melt extruding or injection molding or hot pressing the thermoplastic polymer and the inorganic storage phosphor material to form a melt extruded or injection molded or hot pressed inorganic storage phosphor layer.

In a further aspect, there is disclosed an exemplary re-cycled inorganic storage phosphor panel that can include an inorganic storage phosphor layer including at least one polymer, an inorganic storage phosphor material, and a copper phthalocyanine based blue dye.

In a further aspect, there is disclosed an exemplary method for recycling an inorganic storage phosphor panel that can include providing an inorganic storage phosphor panel comprising at least one polymer, an inorganic storage phosphor material, and a copper phthalocyanine based blue dye; mechanical grinding the inorganic storage phosphor panel into a powder or flakes; melt extruding, injection molding or hot pressing the ground powder or flakes to form a recycled manufactured inorganic storage phosphor panel.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

Figure 1A:
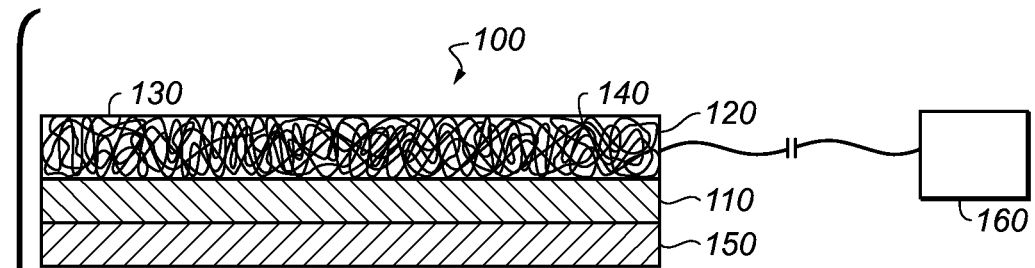
FIGS. 1A-1C depicts exemplary portions of scintillator panels in accordance with various embodiments of the present disclosure.

The following is a description of exemplary embodiments, reference being made to the drawings in which the same reference numerals identify the same elements of structure in each of the several figures.

Exemplary embodiments herein provide storage phosphor panels including an extruded storage phosphor layer with a thermoplastic polymer and a storage phosphor material, and methods of preparing thereof. It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

An important property of the screen is its x-ray absorbance. Depending on the specific application (orthopedic or mammography or intra-oral dental or extra oral dental or non-destructive testing of metals or . . . ), the energy and the intensity of the radiation that is incident on the storage phosphor screen will be different. However, in order to be value as an x-ray imaging tool, the storage phosphor screen has to have sufficient x-ray absorbance, so as to produce a useful image. In practical terms, this requires that ~40-60% of the extruded storage phosphor screen (by volume) be the storage phosphor material (barium fluorobromoiodide or cesium bromide).

Another requirement for the storage phosphor screen is that it be readable from either side of the screen, and in the transmission mode or the reflection mode, with respect to the direction of incidence of the stimulation radiation used for reading the information in the screen. And it would desirable that the screen can be handled under ambient lighting conditions or room light.

Depending on the specific imaging application (medical radiography or dental radiography or non-destructive testing), the physical characteristics required of the storage phosphor panel can be widely different. However, the divergent physical properties may be defined by a few key properties of the storage phosphor screen, such as its bending resistance (see www.taberindustries.com), tear resistance (see www.jlwinstruments.com) or folding resistance (see www.testingmachines.com). A summary of various methods to measure these properties is outlined in the Prediction of Fold Cracking Propensity through Physical Testing.pdf document (see www.gatech.edu). All this may be achieved using a single layer or a multi layered architecture, that would include additional, coextruded layers on the screen, which may contain particulates and/or chemistry to achieve the required physical properties needed to accommodate the mechanics of the scanner and/or handling by the end user. Further, it is important that the extruded storage phosphor screen be recyclable; i.e., it is necessary that the composition of the screen is such that they can re-used to make the storage phosphor screen, and/or the storage phosphor part of the screen can be reused to manufacture a new screen.

The stimulation wavelength and the emission wavelength of the storage phosphor panel are generally determined by the specific storage phosphor. The peak stimulation wavelength for the commonly used storage phosphors, the stimulation wavelength is fairly broad, and is in the region of 550-700 nm. However, the stimulated emission for the europium doped barium fluorobromoiodide storage phosphor has peak around 390 nm.

Figure 1B:
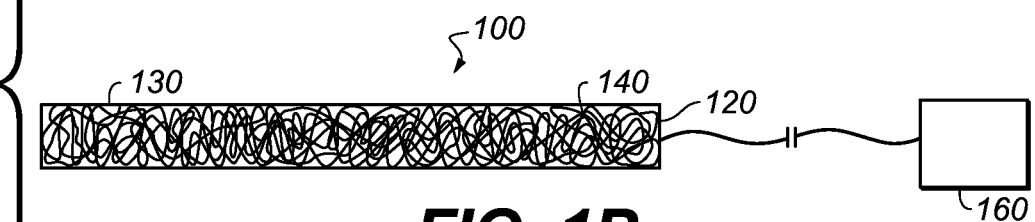
Figure 1C:
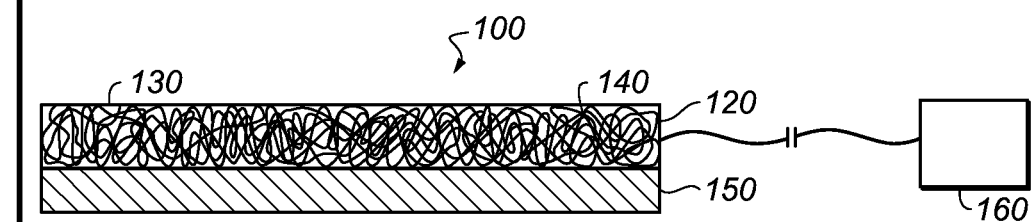

FIG. 1 depicts a portion of an exemplary storage phosphor panel 100 in accordance with various embodiments of the present disclosure. As used herein, "storage phosphor panel" is understood to have its ordinary meaning in the art unless otherwise specified, and refers to panels or screens that store the image upon exposure to X-radiation and emit light when stimulated by another (generally visible) radiation. As such, "panels" and "screens" are used interchangeably herein. It should be readily apparent to one of ordinary skill in the art that the storage phosphor panel 100 depicted in FIGS. 1A-1C represents a generalized schematic illustration and that other components can be added or existing components can be removed or modified.

Storage phosphor panels disclosed herein can take any convenient form provided they meet all of the usual requirements for use in computed radiography. As shown in FIG. 1A, the storage phosphor panel 100 may include a support 110 and a melt extruded or injection molded or hot pressed storage phosphor layer 120 disposed over the support 110. Any flexible or rigid material suitable for use in storage phosphor panels and does not interfere with the recyclability of storage phosphor screen can be used as the support 110, such as glass, plastic films, ceramics, polymeric materials, carbon substrates, and the like. In certain embodiments, the support 110 can be made of ceramic, (e.g., $Al_2O_3$) or metallic (e.g., Al) or polymeric (e.g., polypropylene) materials. Also as shown in FIG. 1A, in an aspect, the support 110 can be coextruded with the storage phosphor layer 120. The support may be transparent, translucent, opaque, or colored (e.g., containing a blue or a black dye). Alternatively, if desired, a support can be omitted in the storage phosphor panel.

In another aspect, an anticurl layer may be coextruded on either side of the support, if a support is used, or on side of the storage phosphor screen, to manage the dimensional stability of the storage phosphor screen.

The thickness of the support 110 can vary depending on the materials used so long as it is capable of supporting itself and layers disposed thereupon. Generally, the support can have a thickness ranging from about 50 µm to about 1,000 µm, for example from about 80 µm to about 1000 µm, such as from about 80 µm to about 500 µm. The support 110 can have a smooth or rough surface, depending on the desired application. In an embodiment, the storage phosphor panel does not comprise a support.

The storage phosphor layer 120 can be disposed over the support 110, if a support is included. Alternatively, the storage phosphor layer 120 can be melt extruded or injection molded or hot pressed independently as shown in FIG. 1B, or melt extruded or injection molded or hot pressed together with an opaque layer, and anticurl layer, and combinations thereof, e.g., shown as layer 150, in FIG. 1A and FIG. 1C.

The storage phosphor layer 120 can include a thermoplastic polymer 130 and a storage phosphor material 140. The thermoplastic polymer 130 may be a polyolefin, such as polyethylene, a polypropylene, and combinations thereof, or a polyurethane, a polyester, a polycarbonate, a silicone, a siloxane, a polyvinyl chloride (PVC), a polyvinylidine chloride (PVdC). In an aspect, the polyethylene can be high density poly low density polyethylene (LDPE), medium density polyethylene (MDPE), linear low density polyethylene (LLDPE), very low density polyethylene (VLDPE), and the like. In a preferred embodiment, the thermoplastic polymer 130 is low density polyethylene (LDPE). The thermoplastic polymer 130 can be present in the storage phosphor layer 120 in an amount ranging from about 1% to about 50% by volume, for example from about 10% to about 30% by volume, relative to the total volume of the storage phosphor layer 120.

As used herein, "storage phosphor particles" and "stimulable phosphor particles" are used interchangeably and are understood to have the ordinary meaning as understood by those skilled in the art unless otherwise specified. "Storage phosphor particles" or "stimulable phosphor particles" refer to phosphor crystals capable of absorbing and storing X-rays and emitting electromagnetic radiation (e.g., light) of a second wavelength when exposed to or stimulated by radiation of still another wavelength. Generally, stimulable phosphor particles are turbid polycrystals having particle diameters of several micrometers to several hundreds of micrometers; however, fine phosphor particles of submicron to nano sizes have also been synthesized and can be useful. Thus, the optimum mean particle size for a given application is a reflection of the balance between imaging speed and desired image sharpness.

Stimulable phosphor particles can be obtained by doping, for example, rare earth ions as an activator into a parent material such as oxides, nitrides, oxynitrides, sulfides, oxysulfides, silicates, halides, and the like, and combinations thereof. As used herein, "rare earth" refers to chemical elements having an atomic number of 39 or 57 through 71 (also known as "lanthanoids"). Stimulable phosphor particles are capable of absorbing a wide range of electromagnetic radiation. In exemplary preferred embodiments, stimulable phosphor particles can absorb radiation having a wavelength of from about 0.01 to about 10 nm (e.g., X-rays) and from about 300 nm to about 1400 nm (e.g., UV, visible, and infrared light). When stimulated with stimulating light having a wavelength in the range of visible and infrared light, stimulable phosphor particles can emit stimulated light at a wavelength of from about 300 nm to about 650 nm.

Suitable exemplary stimulable phosphor particles for use herein include, but are not limited to, compounds having Formula (I):

$$MFX_{1-z}L_{u}M^{a}X^{a}{:}yA{:}eQ{:}tD \qquad (I)$$

wherein M is selected from the group consisting of Mg, Ca, Sr, Ba, and combinations thereof;

X is selected from the group consisting Cl, Br, and combinations thereof;

$M^a$ is selected from the group consisting of Na, K, Rb, Cs, and combinations thereof;

$X^a$ is selected from the group consisting of F, Cl, Br, I, and combinations thereof;

A is selected from the group consisting of Eu, Ce, Sm, Th, Bi, and combinations thereof;

Q is selected from the group consisting of BeO, MgO, CaO, SrO, BaO, ZnO, $Al_2O_3$, $La_2O_3$, $In_2O_3$, $SiO_2$, $TiO_2$, $ZrO_2$, $GeO_2$, $Nb_2O_5$, $Ta_2O_5$, $ThO_2$, and combinations thereof;

D is selected from the group consisting of V, Cr, Mn, Fe, Co, Ni, and combinations thereof;

z is from about 0.0001 to about 1;

u is from about 0 to about 1;

y is from about 0.0001 to about 0.1;

e is from 0 to about 1; and t is from 0 to about 0.01.

The amounts represented by "z", "u", "y", "e", and "t" are molar amounts. The same designations appearing elsewhere in this disclosure have the same meanings unless otherwise specified. In Formula (I), preferably, M is Ba; X is Br; $M^a$ is selected from the group consisting of Na, K, and combinations thereof; $X^a$ is selected from the group consisting of F, Br, and combinations thereof; A is Eu; Q is selected from the group consisting of $SiO_2$, $Al_2O_3$, and combinations thereof; and t is 0.

Other exemplary stimulable phosphor particles for use herein include, but are not limited to, compounds having Formula (II):

$$(Ba_{1-a-b-c}Mg_aCa_bSr_c)FX_{1-z}L_{z}rM^{a}X^{a}{:}yA{:}eQ{:}tD \qquad (II)$$

wherein X, $M^a$, $X^a$, A, Q, D e, t, z, and y are as defined above for Formula (I); the sum of a, b, and c, is from 0 to about 0.4; and r is from about $10^{-6}$ to about 0.1.

In Formula (II), preferably X is Br; $M^a$ is selected from the group consisting of Na, K, and combinations thereof; $X^a$ is selected from the group consisting of F, Br, and combinations thereof; A is selected from the group consisting of Eu, Ce, Bi, and combinations thereof; Q is selected from the group consisting of $SiO_2$, $Al_2O_3$, and combinations thereof; and t is 0.

Further exemplary stimulable phosphor particles for use herein include, but are not limited to, compounds having Formula (III):

$$M^{1+}X_aM^{2+}X'_2bM^{3+}X''3{:}cZ \qquad (III)$$

wherein M is selected from the group consisting of Li, na, K, Cs, Rb, and combinations thereof;

$M^{2+}$ is selected from the group consisting of Be, Mg, Ca, Sr, Ba, Zn, Cd, Cu, Pb, Ni, and combinations thereof;

$M^{3+}$ is selected from the group consisting of Sc, Y, La, Ce, Pr, Nd, Pm, Sm, Eu, Gd, Tb, Dy Ho, Er, Tm Yb, Lum Al, Bi, In, Ga, and combinations thereof;

Z is selected from the group consisting of $Ga^{1+}$, $Ge^{2+}$, $Sn^{2+}$, $Sb^{3+}$, $As^{3+}$, and combinations thereof;

X, X' and X'' can be the same or different and each individually represents a halogen atom selected from the group consisting of F, Br, Cl, I; and $0 \le a \le 1$; $0 \le b \le 1$; $0 < c \le 0.2$.

Preferred stimulable phosphor particles represented by Formulas (I), (II), or (III) include europium activated barium fluorobromides (e.g., BaFBr:Eu and BaFBrI:Eu), cerium activated alkaline earth metal halides, cerium activated oxyhalides, divalent europium activated alkaline earth metal fluorohalides, (e.g., $Ba(Sr)FBr:Eu^{2+}$) divalent europium activated alkaline earth metal halides, rare earth element activated rare earth oxyhalides, bismuth activated alkaline metal halide phosphors, and combinations thereof.

An alternative to the Eu doped BaFBrI type storage phosphor is, Eu doped CsBr storage phosphor. This is generally used in the form a binderless storage phosphor screen, where the needle shaped Eu doped CsBr particles are generated by vapor deposition of the material on a substrate, which is then sealed water impermeable material. Such needle shaped europium doped cesium bromide storage phosphor screen has an emission peak around 450 nm.

The thermoplastic polymer and the inorganic storage phosphor material are melt compounded to form composite thermoplastic particles which are then melt extruded or injection molded or hot pressed to form the inorganic storage phosphor layer. For example, the composite thermoplastic particles can be prepared by melt compounding the thermoplastic polymer with the inorganic storage phosphor material using a twin screw compounder. The ratio of thermoplastic polymer to inorganic storage phosphor material (polymer:inorganic storage phosphor) can range from about 1:100 to about 1:0.01, by weight or volume, preferably from about 1:1 to about 1:0.1, by weight or volume. The composition may include inorganic, organic and/or polymeric additives to manage image quality and/or the physical properties of the extruded storage phosphor screen. Examples of the additives include, a blue dye (e.g., ultramarine blue, copper phthalocyanine, . . . ) for managing image quality, surfactants (e.g., sodium dodecyl sulfate) for managing the colloidal stability of the storage phosphor particles, polymers (e.g., ethylene vinylacetate) for managing the rheology of the composite. During melt compounding, the thermoplastic polymer and the inorganic storage phosphor material can be compounded and heated through multiple heating zones. For example, in the case of polyolefins, the temperature of the heating zones can vary from ca. 170° C.-250° C., depending on the specific composition of the polymer/additive blends that are used, and the period of time in each zone depends on the polymer used and the temperature of the heating zone. Generally, the polymer can be heated for a time and temperature sufficient to melt the polymer and incorporate the inorganic storage phosphor material without decomposing the polymer. The period of time in each zone can range from about 1 second to about 1 minute. In one exemplary embodiment, measured blue dye is added first to the polymer before compounding with storage phosphor particles. Upon exiting the melt compounder, the composite thermoplastic material can enter a water bath to cool and harden into continuous strands. The strands can be pelletized and dried at about 40° C. The screw speed and feed rates for each of the thermoplastic polymer 130 and the inorganic storage phosphor material 140 can be adjusted as desired to control the amount of each in the composite thermoplastic material.

Alternatives to melt compounding include the creation of the composite mixture in an appropriate solvent where the polymer is dissolved or dispersed and inorganic storage phosphor particles are dispersed, followed by the evaporation of the solvent and the milling of the polymer/inorganic storage phosphor composite mixture is pelletized using grinders, cryo-grinder, densifiers, agglomerators, or any other suitable device.

The inorganic storage phosphor/thermoplastic polymer composite material can be melt extruded or injection molded or hot pressed to form the inorganic storage phosphor layer in which the inorganic storage phosphor material is intercalated ("loaded") within the thermoplastic polymer. For example, the inorganic storage phosphor/thermoplastic polymer composite layer can be formed by melt extruding or injection molding or hot pressing the composite thermoplastic material. Without being limited by theory, it is believed that forming the inorganic storage phosphor/thermoplastic composite layer by melt extrusion or injection molding or hot pressing increases the homogeneity of the inorganic storage phosphor layer, and eliminates the undesirable "evaporated space" generated when the solvent is evaporated in the traditional solvent-coated panels. A melt extruded or injection molded or hot pressed inorganic storage phosphor/thermoplastic composite panel according to the present disclosure can have comparable image quality, as compared to the traditional solvent coated panels, along with improved mechanical and environmental robustness.

In the case of the inorganic storage phosphor/thermoplastic polymer composite layer being melt extruded or injection molded or hot pressed in combination with a support layer, the melt processing parameters (temperature, screw speed and pump speed in the case of melt extrusion and injection molding, and temperature and pressure in the case of hot pressing) can be adjusted to control the thickness for each of the inorganic storage phosphor/thermoplastic polymer composite layer and the support layer, individually.

The thickness of the inorganic storage phosphor/thermoplastic composite layer can range from about 10 µm to about 1000 µm, preferably from about 50 µm to about 750 µm, more preferably from about 100 µm to about 500 µm.

Optionally, the melt extruded or injection molded or hot pressed inorganic storage phosphor panel can include a protective overcoat disposed over the inorganic storage phosphor/thermoplastic composite layer, which provides enhanced mechanical strength and scratch and moisture resistance, if desired.

In an embodiment, a scintillation detection system can include the disclosed storage phosphor panel 100 coupled, inserted or mounted to at least one storage phosphor panel reader/scanner 160. Choice of a particular storage phosphor reader will depend, in part, on the type of storage phosphor panel being fabricated and the intended use of the ultimate device used with the disclosed storage phosphor panel.

Image Quality Assessment

The image quality assessments were done as described below. The x-ray source was a Carestream Health CS2200 x-ray generator and the images were scanned using a Carestream Health CS7600 intra oral dental scanner, in the super high resolution mode. The screens were subjected to an x-ray exposure of 70 kV, 7 mA, 0.16 sec. The pixel values were obtained using a flat field exposure of the storage phosphor screen and the resolution was obtained by imaging a line pair phantom, and visual observation. Image quality assessments obtained herein provide a measureable line pairs per mm resolution consistently or across a set or batch of manufactured panels (e.g., an average resolution). For a constant x-ray exposure, fixed scanner conditions, the pixel value represents the efficiency of the storage phosphor screen in converting the incident x-ray photons to optical photons by photostimulated luminescence, which is detected by the detector and converted into digital signals (e.g., code values). As a result, the differences in the pixel code value (cv) represent the differences in the efficiency between the storage phosphor screens.

Comparative Example 1 (Solvent Coated Screen—No Blue Dye)

A solvent coated storage phosphor panel was prepared by mixing a BFBI:Eu phosphor with a solvent package and a binder. The solvent package is prepared by mixing 78 grams of Methylene chloride, 6 grams of Methanol, and 15 grams of 1,3 Dioxolane. The binder is Permuthane (Stahl, Peabody Mass.), which is diluted to 15% in a solvent package listed above. The other ingredients are added to the weight percentage as specified. The film stabilizer (tetrabutyl ammonium thiosulfate) is a 20% solution that is added to help prevent iodide formation in both the liquid and coated state.

| Component | Weight Percentage |
| --- | --- |
| Permuthane Solution | 4.185 |
| Methylene chloride | 26.037 |
| Methanol | 2.013 |
| 1,3 Dixolane | 4.495 |

| Component | Weight Percentage |
|---|---|
| Film Stabilizer | 0.357 |
| Phosphor | 62.457 |
| Total | 100.0 |

The overcoat layer consists of a mixture of 82% Ethyl Acetate and 18% of a copolyester (Vitel 2700B by Bostik Americas). The phosphor solution was coated onto a PET base support and dried using heated air sections to flash off the solvents, with a resultant phosphor coverage of 41 g/ft$^2$. The overcoat solutions were coated on top of the phosphor layer and dried using heated air sections to flash off the solvents, with a resultant overcoat coverage of 0.65 g/ft2.

Comparative Example 2 (Solvent Coated Screen—1200 ppm Ultramarine Blue Dye)

A solvent coated storage phosphor panel was prepared by mixing a BFBI:Eu phosphor with a solvent package and a binder. The solvent package is prepared by mixing 78 grams of Methylene chloride, 6 grams of Methanol, and 15 grams of 1,3 Dioxolane. The binder is Permuthane (Stahl, Peabody Mass.), which is diluted to 15% in a solvent package listed above. The other ingredients are added to the weight percentage as specified. The film stabilizer (tetrabutyl ammonium thiosulfate) is a 20% solution that is added to help prevent iodide formation in both the liquid and coated state. The blue dye (AquaMarine blue from Nubiola) is added at a level equivalent to 1200 ppm based on phosphor weight.

| Component | Percentage |
|---|---|
| Permuthane Solution | 4.063 |
| Methylene chloride | 27.25 |
| Methanol | 2.15 |
| 1,3 Dioxalane | 5.25 |
| Dowanol PM | 0.35 |
| Film Stabilizer | 0.35 |
| UltraMarine Blue | 0.073 |
| Phosphor | 60.526 |
| Total | 100.0 |

The overcoat layer consists of a mixture of Ethyl acetate, Acetone, Methyl methacrylate polymer (Elvacite 2051), 1-Propene, 1,1,2,3,3,3-hexafluoro-polymer with 1,1-difluoroethene (Superflex 2500-20), N,N-Ethylenebis(stearamide) (Superslip 6350), and polymethyl methacrylate matte beads. The ratio of components for the solution is listed below:

| Component | Percentage |
|---|---|
| Ethyl Acetate | 67.875 |
| Acetone | 22.625 |
| Superflex 2500-20 | 2.74 |
| Elvacite 2051 | 6.39 |
| SuperSlip 6350 | 0.183 |
| polymethyl methacrylate matte bead | 0.183 |
| Total | 100.0 |

The phosphor solution was coated onto a PET base support and dried using heated air sections to flash off the solvents, with a resultant phosphor coverage 41 g/ft$^2$. The overcoat solutions were coated on top of the phosphor layer and dried using heated air sections to flash off the solvents, with a resultant overcoat coverage of nominally 0.65 g/ft2.

Comparative Example 3 (Extruded Screen—No Blue Dye)

Composite Thermoplastic Particle Production

Inorganic storage phosphor/thermoplastic composite pellets according to the present disclosure were prepared comprising 80% wt. barium flurobromoiodide (BFBrI) and 20% wt low density polyethylene (LDPE EM811A, available from Westlake Longview Corp. of Houston, Tex.). The die temperature was set to 220° C. and 10 heating zones within the compounder were set to the temperatures shown in Table 1 below:

TABLE 1

| | Zone | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the inorganic storage phosphor/thermoplastic composite pellets, comprising LDPE loaded with BFBrI, entered a 25° C. water bath to cool and hardened into continuous strands. The strands were then fed into a pelletizer and dried at 40° C.

Extrusion or Hot Pressing of Inorganic Storage Phosphor Layer

The pelletized composite thermoplastic materials were loaded into a single screw Davis Standard extruder. Within the extruder, heating zones were set to the temperatures shown in Table 2

TABLE 2

| Davis Extruder | |
|---|---|
| Zone | Temp |
| 1 | 390° F. |
| 2 | 400° F. |
| 3 | 430° F. |
| 4 | 430° F. |
| Gate | 430° F. |
| Adapter | 430° F. |
| Poly line | 430° F. |
| Melt pump | 430° F. |

The pelletized material (composite thermoplastic) was extruded through a single die with the die temperature set at 430° F. form an extruded inorganic storage phosphor panel in the thickness range of 100-200 microns.

In some cases, the pellets were heat pressed into a flat sheet by placing compounded pellets between 2 plates and applying pressure up to 15,000 psig. using a Carver Hydraulic Press Model C. The plates were heated to approximately 220° C. The plates were pressed together for a timeframe between 30 and 60 seconds.

Comparative Example 4 (Extruded Screen—1000 ppm Ultramarine Blue Dye)

Composite Thermoplastic Particle Production

A sample was prepared as described in comparative example 3, with the difference that the formulation included a blue dye (ultramarine blue) at a level of 1000 ppm with respect to the weight of the phosphor.

A 0.5% concentration of 65561-A Ultramarine blue in LDPE EM 811AA was used to create 1000 ppm blue dye concentration in the final inorganic storage phosphor/thermoplastic polymer composite. In order to achieve this, the undyed EM811A polymer resin and the dyed (0.5% blue) EM811A masterbatch were blended and compounded with the BFBrI powder using a Leistritz twin screw compounder. The die temperature was set to 220° C. and 10 heating zones within the compounder were set to the temperatures shown in Table 3 below:

TABLE 3

| | Zone | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the composite thermoplastic particles, comprising of 1000 ppm blue dyed LDPE loaded with BFBrI, entered a 25° C. water bath to cool and hardened into continuous strands. The strands were then pelletized in a pelletizer and dried at 40° C.

Extrusion or Hot Pressing of Inorganic Storage Phosphor Layer

The pelletized composite thermoplastic materials were loaded into a single screw Davis Standard extruder. Within the extruder, heating zones were set to the temperatures shown in Table 4

TABLE 4

| Davis Standard Extruder | |
|---|---|
| Zone | Temp |
| 1 | 390° F. |
| 2 | 400° F. |
| 3 | 430° F. |
| 4 | 430° F. |
| Gate | 430° F. |
| Adapter | 430° F. |
| Poly line | 430° F. |
| Melt pump | 430° F. |

The pelletized material (composite thermoplastic) was extruded through a single die with the die temperature set at 430° F. to form an extruded inorganic storage phosphor panel in the thickness range of 100-200 microns.

In some cases, the pellets were heat pressed into a flat sheet by placing compounded pellets between 2 plates and applying pressure up to 15,000 psig, using a Carver Hydraulic Press Model C. The plates were each heated to approximately 220° C. The plates were pressed together for a timeframe between 30 and 60 seconds.

Inventive Example 1 (Hot Pressed Screen—100 ppm Copper Phthalocyanine Blue Dye)

Composite Thermoplastic Particle Production

A sample was prepared as described in comparative example 3, with the difference that the formulation included a blue dye (copper phthalocyanine) at a level of 100 ppm with respect to the weight of the phosphor.

The inventors understand that hundreds of potential blue dye materials exist that can be used with stimulable storage phosphor panels. However, the inventors have determined that only specific selected blue dyes improve resolution with exemplary inventive method and/or apparatus embodiments according to the application. For example, the inventors determined copper phthalocyanine based blue dye improves resolution for inventive method and/or apparatus embodiments described herein.

A 10% concentration of 65530-A Trans Blue (copper phthalocyanine) in LDPE EM 811AA was diluted step wise to a concentration of 1% with the LDPE EM811A, available from Westlake Longview Corp. of Houston, Tex. To achieve the 100 ppm blue dye concentration in the final inorganic storage phosphor/thermoplastic polymer composite, the undyed EM811A polymer resin and the dyed (1% blue) EM811A masterbatch were blended and compounded with the BFBrI powder using a Leistritz twin screw compounder. The die temperature was set to 220° C. and 10 heating zones within the compounder were set to the temperatures shown in Table 5 below:

TABLE 5

| | Zone | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the composite thermoplastic particles, comprising of 100 ppm blue dyed LDPE loaded with BFBrI, entered a 25° C. water bath to cool and hardened into continuous strands. The strands were then pelletized in a pelletizer and dried at 40° C.

Extrusion or Hot Pressing of Inorganic Storage Phosphor Layer

The pelletized composite thermoplastic materials were loaded into a single screw Davis Standard extruder. Within the extruder, heating zones were set to the temperatures shown in Table 6.

TABLE 6

Davis Standard Extruder

| Zone | Temp |
| --- | --- |
| 1 | 390° F. |
| 2 | 400° F. |
| 3 | 430° F. |
| 4 | 430° F. |
| Gate | 430° F. |
| Adapter | 430° F. |
| Poly line | 430° F. |
| Melt pump | 430° F. |

The pelletized material (composite thermoplastic) was extruded through a single die with the die temperature set at 430° F. form an extruded inorganic storage phosphor panel in the thickness range of 100-200 microns.

In some cases, the pellets were heat pressed into a flat sheet by placing compounded pellets between 2 plates and applying pressure up to 15,000 psig, using a Carver Hydraulic Press Model C. The plates were each heated to approximately 220° C. The plates were pressed together for a timeframe between 30 and 60 seconds.

Inventive Example 2 (Hot Pressed Screen—200 ppm Copper Phthalocyanine Blue Dye)

Composite Thermoplastic Particle Production

A sample was prepared as described in inventive example 1, with the difference that the formulation included a blue dye (copper phthalocyanine) at a level of 200 ppm with respect to the weight of the phosphor.

Extrusion or Hot Pressing of Inorganic Storage Phosphor Layer

The pelletized composite thermoplastic materials were loaded into a single screw Davis Standard extruder. Within the extruder, heating zones were set to the temperatures shown in Table 7.

TABLE 7

Davis Standard Extruder

| Zone | Temp |
| --- | --- |
| 1 | 390° F. |
| 2 | 400° F. |
| 3 | 430° F. |
| 4 | 430° F. |
| Gate | 430° F. |
| Adapter | 430° F. |
| Poly line | 430° F. |
| Melt pump | 430° F. |

The pelletized material (composite thermoplastic) was extruded through a single die with the die temperature set at 430° F. form an extruded inorganic storage phosphor panel in the thickness range of 100-200 microns.

In some cases, the pellets were heat pressed into a flat sheet by placing compounded pellets between 2 plates and applying pressure up to 15,000 psig, using a Carver Hydraulic Press Model C. The plates were each heated to approximately 220° C. The plates were pressed together for a timeframe between 30 and 60 seconds.

The inventors have determined that in exemplary method and/or apparatus embodiments according to the application disclosed herein that using a copper phthalocyanine based blue dye at levels above 200 parts per million began to negatively impact image quality by reducing signal levels (e.g., reducing emission throughput).

The comparative and inventive examples were characterized as described above.

ANALYSIS 1

| | Relative Screen Efficiency (pixel code values) | Resolution (LP/mm) |
| --- | --- | --- |
| Comparative example 1 (Solvent coated screen - no blue dye) | 3568 | 14 |
| Comparative example 2 (Solvent coated screen - 1200 ppm ultramarine blue dye) | 3295 | 17 |
| Comparative example 3 (Extruded screen - no blue dye) | 3290 | 14 |
| Comparative example 4 (Extruded screen - 1000 ppm ultramarine blue dye) | 3195 | 14 |
| Inventive example 1 (Hot pressed screen - 100 ppm copper phthalocyanine blue dye) | 3162 | 18 |
| Inventive example 2 (Hot pressed screen - 200 ppm copper phthalocyanine blue dye) | 2956 | 19 |

Exemplary method and/or apparatus embodiments can provide inorganic storage phosphor panels including an inorganic storage phosphor layer including at least one thermoplastic polyolefin, an inorganic storage phosphor material and a blue dye, where the storage phosphor layer has a resolution of >15 lp/mm, where the blue dye is at least 50% reduced in amount from a conventional solvent coated inorganic storage phosphor screen having similar resolution. In certain exemplary embodiments, the inorganic storage phosphor panel has an image resolution greater than 16 lp/mm. greater than 17 lp/mm. greater than 18 lp/mm, greater than 19 lp/mm, or greater than 20 lp/mm. In certain exemplary embodiments, the blue dye is at least 60% reduced in amount, at least 70% reduced in amount, at least 80% reduced in amount, or at least 90% reduced in amount from a conventional solvent coated inorganic storage phosphor screen having similar resolution.

Exemplary method embodiments using an inorganic storage phosphor panel can include melt extruding, injection molding or hot pressing materials comprising at least one thermoplastic polyolefin, an inorganic storage phosphor material and a blue dye to form an extruded inorganic storage phosphor layer, where the storage phosphor layer has a resolution of >15 lp/mm, where the blue dye is at least 50% reduced in amount from a conventional solvent coated inorganic storage phosphor screen having similar resolution; exposing the extruded inorganic storage phosphor layer to x-rays to form a latent image; and exposing the latent image in the extruded inorganic storage phosphor layer to excitation light to generate a digital image of the latent image.

Certain exemplary method and/or apparatus embodiments can provide inorganic storage phosphor panels including an inorganic storage phosphor layer including at least one thermoplastic polyolefin, an inorganic storage phosphor material and a blue dye, where the storage phosphor layer has a resolution of >19 lp/mm, resolution of >20 lp/mm, or resolution of >21 lp/mm.

In selected exemplary embodiments, the inorganic storage phosphor panels are formed by melt extruding, injection molding or hot pressing.

Certain exemplary method and/or apparatus embodiments can provide inorganic storage phosphor panels where the relative screen efficiency loss is less than 15%, less than 25%, less than 40% compared to a storage phosphor panel without blue dye.

Certain exemplary method and/or apparatus embodiments can provide a thermoplastic polyolefin storage phosphor screen which has a resolution of >15 lp/mm, a resolution of >16 lp/mm, a resolution of >17 lp/mm, a resolution of >18 lp/mm, a resolution of >19 lp/mm, a resolution of >20 lp/mm.

Certain exemplary method and/or apparatus embodiments can provide a thermoplastic storage phosphor screen which has a resolution of >15 lp/mm, a resolution of >16 lp/mm, a resolution of >17 lp/mm, a resolution of >18 lp/mm, a resolution of >19 lp/mm, a resolution of >20 lp/mm.

Certain exemplary method and/or apparatus embodiments can provide a storage phosphor screen which has a resolution of >15 lp/mm, a resolution of >16 lp/mm, a resolution of >17 lp/mm, a resolution of >18 lp/mm, a resolution of >19 lp/mm, a resolution of >20 lp/mm.

In selected exemplary embodiments, the inorganic storage phosphor screen is formed by melt extruding, injection molding or hot pressing.

Certain exemplary method and/or apparatus embodiments can provide an inorganic storage phosphor panel including an inorganic storage phosphor layer including at least one thermoplastic polyolefin, an inorganic storage phosphor material and a copper phthalocyanine based blue dye, wherein the inorganic storage phosphor panel has a image resolution greater than 15 lp/mm, greater than 16 lp/mm. greater than 17 lp/mm. greater than 18 lp/mm, greater than 19 lp/mm, or greater than 20 lp/mm. In selected exemplary embodiments, the inorganic storage phosphor layer is formed by melt extruding, injection molding or hot pressing.

Certain exemplary method and/or apparatus embodiments can provide an inorganic storage phosphor panel including an inorganic storage phosphor layer including at least one thermoplastic polyolefin, an inorganic storage phosphor material and a blue dye between $1\times10^2$ and $3\times10^2$ ppm, wherein the inorganic storage phosphor panel has a image resolution greater than 18 lp/mm. Certain exemplary method and/or apparatus embodiments can provide an inorganic storage phosphor panel including an inorganic storage phosphor layer including at least one thermoplastic polyolefin, an inorganic storage phosphor material and a copper phthalocyanine based blue dye, wherein the inorganic storage phosphor panel has a image resolution greater than 15 lp/mm, greater than 16 lp/mm. greater than 17 lp/mm. greater than 18 lp/mm, greater than 19 lp/mm, or greater than 20 lp/mm. In selected exemplary embodiments, the inorganic storage phosphor panel is formed by melt extruding, injection molding or hot pressing.

Certain exemplary method embodiments can using an inorganic storage phosphor panel including melt extruding, injection molding or hot pressing materials comprising at least one thermoplastic polyolefin, an inorganic storage phosphor material and a copper phthalocyanine based blue dye between $1\times10^2$ and $3\times10^2$ ppm to form an extruded inorganic storage phosphor layer; exposing the extruded inorganic storage phosphor layer to x-rays to form a latent image; and exposing the latent image in the extruded inorganic storage phosphor layer to excitation light to generate a digital image of the latent image.

In one exemplary embodiment, a latent x-ray image in the storage phosphor screen is read by scanning. In one exemplary embodiment, a latent image in the storage phosphor screen is read using reflectance scanning in a reflectance mode or transmissive scanning in a transmissive mode.

Image Quality Assessment

The image quality assessments were done as described below. The extruded plate is adhered to a black PET (Toray Lumirror X30-10 mil) support using an optically clear adhesive (3M 8141). This plate is then placed in the Carestream CS2200 x-ray generator, and exposed to an x-ray exposure of 70 kV, 7 mA, 0.16 sec. This exposed plate, kept in subdued ambient light, is then scanned in the Carestream Health CS7600 intra oral dental scanner, in the super high resolution mode. The image is saved as a JPEG file and looked at on a computer monitor for defect count. The plates are all dental size 2 with an area of approximately 12.71 $cm^2$.

Applicants have found that inorganic storage phosphor particles disclosed herein suffer nano-particle effects when reaching sizes below 1 micron including increased viscosity, increased surface roughness including holes and recesses on surfaces and/or agglomeration effects.

Comparative Example 5

Composite Thermoplastic Particle Production

Inorganic storage phosphor/thermoplastic composite pellets according to the present disclosure were prepared comprising of 86% wt. barium flurobromoiodide (BFBrI) and 14% wt low density polyethylene (LDPE EM811A, available from Westlake Longview Corp. of Houston, Tex.).

The inorganic storage phosphor particles was characterized using the Microtrac 9200 FRA, to have 95% of the particles to be ≤8.33 microns and 50% of the particles to be ≤4.12 microns in diameter.

The formulation included a blue dye (copper phthalocyanine) at a level of 100 ppm with respect to the weight of the phosphor. A 10% concentration of 65530-A Trans Blue (copper phthalocyanine) in LDPE EM 811AA was diluted step wise to a concentration of 1% with the LDPE EM811A, available from Westlake Longview Corp. of Houston, Tex. To achieve the 100 ppm blue dye concentration in the final inorganic storage phosphor/thermoplastic polymer composite, the undyed EM811A polymer resin and the dyed (1% blue) EM811A masterbatch were blended and compounded with the BFBrI powder using a Leistritz twin screw compounder.

The die temperature was set to 220° C. and 10 heating zones within the compounder were set to the temperatures shown in Table 8 below:

TABLE 8

| | Zone | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the inorganic storage phosphor/thermoplastic composite pellets, comprising LDPE loaded with BFBrI, entered a 25° C. water bath to cool and hardened into continuous strands. The strands were then fed into a pelletizer and dried at 40° C.

Extrusion of Inorganic Storage Phosphor Layer

The pelletized composite thermoplastic materials were loaded into a single screw Davis Standard extruder. Within the extruder, heating zones were set to the temperatures shown in Table 9

TABLE 9

| Davis Extruder | |
|---|---|
| Zone | Temp |
| 1 | 390° F. |
| 2 | 400° F. |
| 3 | 430° F. |
| 4 | 430° F. |
| Gate | 430° F. |
| Adapter | 430° F. |
| Poly line | 430° F. |
| Melt pump | 430° F. |

The pelletized material (composite thermoplastic) was extruded through a single die with the die temperature set at 430° F. form an extruded inorganic storage phosphor panel in the thickness range of 100-200 microns.

Comparative Example 6

Composite Thermoplastic Particle Production

Inorganic storage phosphor/thermoplastic composite pellets according to the present disclosure were prepared comprising 83% wt. barium flurobromoiodide (BFBrI) and 17% wt low density polyethylene (LDPE EM811A, available from Westlake Longview Corp. of Houston, Tex.).

The following differences between comparative example 5 and example 6 is the weight of the phosphor is 86% versus 83%, there is no blue dye, and the inorganic storage phosphor particles as characterized using the Microtrac 9200 FRA, to have 95% of the particles to be ≤7.56 microns and 50% of the particles to be ≤4.20 microns in diameter.

The die temperature was set to 220° C. and 10 heating zones within the compounder were set to the temperatures shown in Table 10 below:

TABLE 10

| | Zone | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the inorganic storage phosphor/thermoplastic composite pellets, comprising LDPE loaded with BFBrI, entered a 25° C. water bath to cool and hardened into continuous strands. The strands were then fed into a pelletizer and dried at 40° C.

Extrusion of Inorganic Storage Phosphor Layer

The pelletized composite thermoplastic materials were loaded into a single screw Davis Standard extruder. Within the extruder, heating zones were set to the temperatures shown in Table 11

TABLE 11

| Davis Standard Extruder | |
|---|---|
| Zone | Temp |
| 1 | 390° F. |
| 2 | 400° F. |
| 3 | 430° F. |
| 4 | 430° F. |
| Gate | 430° F. |
| Adapter | 430° F. |
| Poly line | 430° F. |
| Melt pump | 430° F. |

The pelletized material (composite thermoplastic) was extruded through a single die with the die temperature set at 430° F. form an extruded inorganic storage phosphor panel in the thickness range of 100-200 microns.

Inventive Example 3

Composite Thermoplastic Particle Production

A sample was prepared as described in comparative example 5, with the following differences between comparative example 5 and inventive example 3 is there is no blue dye, and the inorganic storage phosphor particles as characterized using the Microtrac 9200 FRA, to have 95% of the particles to be ≤6.78 microns and 50% of the particles to be ≤3.81 microns in diameter.

The die temperature was set to 220° C. and 10 heating zones within the compounder were set to the temperatures shown in Table 12 below:

TABLE 12

| | Zone | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the composite thermoplastic particles, comprising of LDPE loaded with BFBrI, entered a 25° C. water bath to cool and hardened into continuous strands. The strands were then pelletized in a pelletizer and dried at 40° C.

Extrusion of Inorganic Storage Phosphor Layer

The pelletized composite thermoplastic materials were loaded into a single screw Davis Standard extruder. Within the extruder, heating zones were set to the temperatures shown in Table 13

TABLE 13

| Davis Standard Extruder | |
|---|---|
| Zone | Temp |
| 1 | 390° F. |
| 2 | 400° F. |
| 3 | 430° F. |
| 4 | 430° F. |
| Gate | 430° F. |
| Adapter | 430° F. |
| Poly line | 430° F. |
| Melt pump | 430° F. |

The pelletized material (composite thermoplastic) was extruded through a single die with the die temperature set at 430° F. form an extruded inorganic storage phosphor panel in the thickness range of 100-200 microns.

Inventive Example 4

Composite Thermoplastic Particle Production

A sample was prepared as described in comparative example 5, with the primary differences being: the blue dye (copper phthalocyanine) level is approximately 200 ppm with respect to the weight of the phosphor and the inorganic storage phosphor particles was characterized using the Microtrac 9200 FRA, to have 95% of the particles to be ≤6.00 microns and 50% of the particles to be ≤3.45 microns in diameter.

Extrusion of Inorganic Storage Phosphor Layer

The pelletized composite thermoplastic materials were loaded into a single screw Davis Standard extruder. Within the extruder, heating zones were set to the temperatures shown in Table 14

TABLE 14

| Davis Standard Extruder | |
|---|---|
| Zone | Temp |
| 1 | 390° F. |
| 2 | 400° F. |
| 3 | 430° F. |
| 4 | 430° F. |
| Gate | 430° F. |
| Adapter | 430° F. |

TABLE 14-continued

| Davis Standard Extruder | |
|---|---|
| Zone | Temp |
| Poly line | 430° F. |
| Melt pump | 430° F. |

The pelletized material (composite thermoplastic) was extruded through a single die with the die temperature set at 430° F. form an extruded inorganic storage phosphor panel in the thickness range of 100-200 microns.

The comparative and inventive examples were characterized for defects as described above.

ANALYSIS 2

| | # defects per cm$^2$ |
|---|---|
| Comparative example 5 | ≥30 |
| Comparative example 6 | ≥30 |
| Inventive example 3 | ≤5 |
| Inventive example 4 | ≤5 |

Exemplary method and/or apparatus embodiments can provide free standing inorganic storage phosphor panels that can include an inorganic storage phosphor layer including at least one polymer, an inorganic storage phosphor material, and a blue dye, where the storage phosphor layer has fewer than 5 defects per square cm. Certain exemplary method embodiments can provide methods including combining materials including at least one polymer, an inorganic storage phosphor material and a blue dye to form a manufactured inorganic storage phosphor layer, where the storage phosphor layer has fewer than 5 defects; exposing the manufactured inorganic storage phosphor layer to x-rays to form a latent image; and exposing the latent image in the manufactured inorganic storage phosphor layer to excitation light to generate a digital image of the latent image. In one embodiment, the combining is by melt extruding, injection molding or hot pressing. In one embodiment, a latent image in the storage phosphor screen is read using reflectance scanning in a reflectance mode or transmissive scanning in a transmissive mode. In some embodiments, the polymer is a thermoplastic polyolefin. In some embodiments, the blue dye is a copper phthalocyanine blue dye.

Certain exemplary method embodiments can provide free standing inorganic storage phosphor panels including an inorganic storage phosphor layer including at least one polymer, an inorganic storage phosphor material that has 95% of the particles to be ≤6.8 microns in diameter, and a blue dye, where the storage phosphor layer has fewer than 5 defects per square cm. Certain exemplary method embodiments can provide methods including combining materials including at least one polymer, an inorganic storage phosphor material that has 95% of the particles to be <6.8 microns in diameter and a blue dye to form an extruded inorganic storage phosphor layer, where the storage phosphor layer has fewer than 5 defects; exposing the extruded inorganic storage phosphor layer to x-rays to form a latent image; and exposing the latent image in the extruded inorganic storage phosphor layer to excitation light to generate a digital image of the latent image. In one embodiment, the combining is by melt extruding, injection molding or hot pressing. In one embodiment, a latent image in the storage phosphor screen is read using reflectance scanning in a reflectance mode or transmissive scanning in a transmissive mode. In some embodiments, the polymer is a thermoplastic polyolefin. In some embodiments, the blue dye is a copper phthalocyanine blue dye.

Certain exemplary method embodiments can provide free standing inorganic storage phosphor panels including an inorganic storage phosphor layer including at least one polymer, an inorganic storage phosphor material that has 95% of the particles to be <6.8 microns in diameter, and 50% of the particles to be <3.8 microns in diameter and a blue dye, where the storage phosphor layer has fewer than 5 defects per square cm. Certain exemplary method embodiments can provide methods including combining materials including at least one polymer, an inorganic storage phosphor material that has 95% of the particles to be <6.8 microns in diameter, and 50% of the particles to be <3.8 microns in diameter and a blue dye to form an extruded inorganic storage phosphor layer, where the storage phosphor layer has fewer than 5 defects; exposing the extruded inorganic storage phosphor layer to x-rays to form a latent image; and exposing the latent image in the extruded inorganic storage phosphor layer to excitation light to generate a digital image of the latent image. In one embodiment, the combining is by melt extruding, injection molding or hot pressing. In one embodiment, a latent image in the storage phosphor screen is read using reflectance scanning in a reflectance mode or transmissive scanning in a transmissive mode. In some embodiments, the polymer is a thermoplastic polyolefin. In some embodiments, the blue dye is a copper phthalocyanine blue dye.

Certain exemplary method embodiments can provide free standing inorganic storage phosphor panels including an inorganic storage phosphor layer including at least one polymer, an inorganic storage phosphor material that has 50% of the particles to be <3.8 microns in diameter and a blue dye, where the storage phosphor layer has fewer than 5 defects per square cm. Certain exemplary method embodiments can provide methods including melt extruding, injection molding or hot pressing materials including at least one polymer, an inorganic storage phosphor material that has 50% of the particles to be <3.8 microns in diameter and a blue dye to form an extruded inorganic storage phosphor layer, where the storage phosphor layer has fewer than 5 defects; exposing the extruded inorganic storage phosphor layer to x-rays to form a latent image; and exposing the latent image in the extruded inorganic storage phosphor layer to excitation light to generate a digital image of the latent image. In one embodiment, a latent image in the storage phosphor screen is read using reflectance scanning in a reflectance mode or transmissive scanning in a transmissive mode. In some embodiments, the polymer is a thermoplastic polyolefin. In some embodiments, the blue dye is a copper phthalocyanine blue dye.

Image Quality Assessment

The image quality assessments were done as described below. The extruded plate is adhered to a black PET (Toray Lumirror X30-10 mil) support using an optically clear adhesive (3M 8141). The solvent coated plates already had a PET support, and were not subjected to the adhesion of an additional PET support. This plate is then placed in the Carestream Health CS2200 x-ray generator and exposed to an x-ray exposure of 70 kV, 7 mA, and 0.16 sec. This exposed plate, kept in subdued ambient light, is then scanned in the Carestream Health CS7600 intra oral-dental scanner, in the super high resolution mode. The flat field image is saved as a linearized dicom file. The average linearized pixel value and the standard deviation is calculated using a dicom viewer, and the coefficient of variation (COV) is calculated as the ratio of the standard deviation to the average linearized pixel value.

The plates are all dental size 2 with an area of approximately 12.71 cm$^2$.

Comparative Example 7

A CS7600 intra oral computed radiography plate SN ED005947 was used as a comparative example.

Comparative Example 8

A Durr Dental intra oral computed radiography plate CE 0124 was used as a comparative example.

Comparative Example 9

A solvent coated storage phosphor panel was prepared by mixing a BFBI:Eu phosphor with a solvent package and a binder. The solvent package is prepared by mixing 78 grams of Methylene chloride, 6 grams of Methanol, and 15 grams of 1,3 Dioxolane. The binder is Permuthane (Stahl, Peabody Mass.), which is diluted to 15% in a solvent package listed above. The other ingredients are added to the weight percentage as specified. The film stabilizer (tetrabutyl ammonium thiosulfate) is a 20% solution that is added to help prevent iodide formation in both the liquid and coated state. The blue dye (Ultramarine blue from Nubiola) is added at a level equivalent to 1200 ppm based on phosphor weight.

TABLE 15

| Component | Percentage |
| --- | --- |
| Permuthane Solution | 4.063 |
| Methylene chloride | 27.25 |
| Methanol | 2.15 |
| 1,3 Dixolane | 5.25 |
| Dowanol PM | 0.35 |
| Film Stabilizer | 0.35 |
| UltraMarine Blue | 0.073 |
| Phosphor | 60.526 |
| Total | 100.0 |

The overcoat layer consists of a mixture of Ethyl acetate, Acetone, Methyl methacrylate polymer (Elvacite 2051), 1-Propene, 1,1,2,3,3,3-hexafluoro-polymer with 1,1-difluoroethene (Superflex 2500-20), N,N-Ethylenebis(stearamide) (Superslip 6350), and polymethyl methacrylate matte beads. The ratio of components for the solution is listed below:

TABLE 16

| Component | Percentage |
| --- | --- |
| Ethyl Acetate | 67.875 |
| Acetone | 22.625 |
| Superflex 2500-20 | 2.74 |
| Elvacite 2051 | 6.39 |

TABLE 16-continued

| Component | Percentage |
|---|---|
| SuperSlip 6350 | 0.183 |
| polymethyl methacrylate matte bead | 0.183 |
| Total | 100.0 |

The phosphor solution was coated onto a PET base support and dried using heated air sections to flash off the solvents, with a resultant phosphor coverage 41 g/ft². The overcoat solutions were coated on top of the phosphor layer and dried using heated air sections to flash off the solvents, with resultant overcoat coverage of nominally 0.65 g/ft2.

Comparative Example 10

Composite Thermoplastic Particle Production

Inorganic storage phosphor/thermoplastic composite pellets according to the present disclosure were prepared comprising 86% wt. barium flurobromoiodide (BFBrI) and 14% wt low density polyethylene (LDPE EM811A, available from Westlake Longview Corp. of Houston, Tex.). The inorganic storage phosphor particles was characterized using the Microtrac 9200 FRA, to have 95% of the particles to be <5.97 microns and 50% of the particles to be <3.51 microns in diameter.

The formulation involved blending and compounding of the EM811A polymer resin with the BFBrI powder using a Leistritz GL-400 twin screw compounder. The screw speed was set at 300 RPM. The die temperature was set to 220° C. and 10 heating zones within the compounder were set to the temperatures shown in Table 17 below:

TABLE 17

| Zone | | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the inorganic storage phosphor/thermoplastic composite pellets, comprising LDPE loaded with BFBrI, entered a 25° C. water bath to cool and hardened into continuous strands. The strands were then fed into a pelletizer and dried at 40° C.

Extrusion of Inorganic Storage Phosphor Layer

The pelletized composite thermoplastic materials were loaded into a single screw Killion extruder. Within the extruder, heating zones were set to the temperatures shown in Table 18.

TABLE 18

| Killion Extruder | |
|---|---|
| Zone | Temp |
| 1 | 390° F. |
| 2 | 420° F. |
| 3 | 430° F. |
| 4 | 430° F. |
| Gate | 430° F. |
| Die | 430° F. |

The pelletized material (composite thermoplastic) was extruded through a single die with the die temperature set at 430° F. form an extruded inorganic storage phosphor panel in the thickness range of 100-200 microns.

Inventive Example 5

Composite Thermoplastic Particle Production

A sample was prepared as described in comparative example 10, with the difference that it contained ultramarine blue dye at a level of 1600 ppm with respect to the phosphor.

Inventive Example 6

Composite Thermoplastic Particle Production

A sample was prepared as described in inventive example 5, with a primary difference being the blue dye is copper phthalocyanine instead of ultramarine blue, at a level of approximately 12.5 ppm with respect to the phosphor.

Inventive Example 7

Composite Thermoplastic Particle Production

A sample was prepared as described in inventive example 5, with a primary difference being the blue dye is copper phthalocyanine instead of ultramarine blue, at a level of approximately 50 ppm with respect to the phosphor.

Inventive Example 8

Composite Thermoplastic Particle Production

A sample was prepared as described in inventive example 5, with a primary difference being the blue dye is copper phthalocyanine instead of ultramarine blue, at a level of approximately 50 ppm with respect to the phosphor, and the use of a polymer processing additive (PSA), Kynar Superflex® 2500-20, from Arkema, at a level of 1000 ppm with respect to the phosphor.

| ANALYSIS 3 | | | | |
|---|---|---|---|---|
| Sample | Average Speed | Std. Dev. | Noise (coefficient of variation CV) | Relative CV (with respect to comparative example 7) |
| Comparative Example 7 | 53055 | 326 | 0.61% | 100% |
| Comparative Example 8 | 53991 | 274 | 0.51% | 83% |
| Comparative Example 9 | 53966 | 332 | 0.62% | 100% |
| Comparative Example 10 | 54266 | 336 | 0.62% | 101% |
| Inventive Example 5 | 56281 | 231 | 0.41% | 67% |
| Inventive Example 6 | 55918 | 239 | 0.43% | 70% |
| Inventive Example 7 | 58903 | 163 | 0.28% | 45% |
| Inventive Example 8 | 59460 | 121 | 0.20% | 33% |

In certain exemplary method and/or apparatus embodiments, the copper phthalocyanine blue dye is configured to reduce noise effects.

Exemplary method and/or apparatus embodiments can provide free standing inorganic storage phosphor panels that can include an inorganic storage phosphor layer including at least one polymer, an inorganic storage phosphor material that has 95% of the particles to be ≤6.8 microns in diameter, and a blue dye, and the inorganic storage phosphor layer has a coefficient of variation in the linearized pixel value that is less than or equal to 0.40.

Exemplary method and/or apparatus embodiments can provide free standing inorganic storage phosphor panels that can include an inorganic storage phosphor layer including at least one polymer or thermoplastic polyolefin, an inorganic storage phosphor material that has 95% of the particles to be ≤6.8 microns in diameter, and 50% of the particles to be ≤3.8 microns in diameter and a blue dye, and has a coefficient of variation in the linearized pixel value that is less than or equal to 0.40.

Exemplary method and/or apparatus embodiments can provide free standing inorganic storage phosphor panels that can include an inorganic storage phosphor layer including at least one polymer, an inorganic storage phosphor material, and a blue dye, where the storage phosphor layer has a coefficient of variation in the linearized pixel value that is less than or equal to 0.40. Certain exemplary method embodiments can provide methods including combining materials including at least one polymer, an inorganic storage phosphor material and a blue dye to form a manufactured inorganic storage phosphor layer, which has a coefficient of variation in the linearized pixel value that is less than or equal to 0.40; exposing the manufactured inorganic storage phosphor layer to x-rays to form a latent image; and exposing the latent image in the manufactured inorganic storage phosphor layer to excitation light to generate a digital image of the latent image. Certain exemplary method embodiments can provide methods including melt extruding, injection molding or hot pressing materials comprising at least one thermoplastic polyolefin, an inorganic storage phosphor material that has 95% of its particles to be ≤6.8 microns in diameter, and 50% of the particles to be ≤3.8 microns in diameter and a blue dye to form a manufactured inorganic storage phosphor layer, which has a coefficient of variation in the linearized pixel value that is less than or equal to 0.40; exposing the manufactured inorganic storage phosphor layer to x-rays to form a latent image; and exposing the latent image in the manufactured inorganic storage phosphor layer to excitation light to generate a digital image of the latent image. In one embodiment, the combining is by melt extruding, injection molding or hot pressing. In one embodiment, a latent image in the storage phosphor screen is read using reflectance scanning in a reflectance mode or transmissive scanning in a transmissive mode. In some embodiments, the polymer is a thermoplastic polyolefin. In some embodiments, the blue dye is a copper phthalocyanine blue dye. In one embodiment, the manufactured inorganic storage phosphor layer has a coefficient of variation in the linearized pixel value that is less than or equal to 70% of that of an equivalent solvent coated storage phosphor screen. In one embodiment, the manufactured inorganic storage phosphor layer has a coefficient of variation in the linearized pixel value that is less than or equal less than or equal to half that of an equivalent solvent coated storage phosphor screen. In certain exemplary embodiments, the inorganic storage phosphor material has 95% of its particles to be ≤6.8 microns in diameter. In certain exemplary embodiments, the inorganic storage phosphor material has 95% of its particles to be ≤6.8 microns in diameter and 95% of the particles to be ≥1.0 microns in diameter. In certain exemplary embodiments, the extruded or manufactured inorganic storage phosphor layer has 95% of its inorganic storage phosphor material particles to be ≤6.8 microns in diameter and 95% of its inorganic storage phosphor material particles to be ≥1.0 microns in diameter.

Assessment

An important characteristic of the melt extruded or injection molded or hot pressed inorganic storage phosphor panel is that it can be recycled and reused by simply grinding (e.g., mechanically or electromechanically) the panels using a standard device such as a grinder, cryo-grinder, densifiers, agglomerators, or any other suitable device, and pelletizing it during the crushing process, and/or subsequently by a compounding processes described above, and extruding it again as a storage phosphor panel. In order to do be able to recycle the melt extruded or injection molded or hot pressed inorganic storage phosphor panel effectively, it is beneficial or necessary that the storage phosphor panel can be ground without abrading the grinding equipment. An important measure of the ability to grind the melt extruded or injection molded or hot pressed inorganic storage phosphor panel panels without abrading the grinding equipment is its fracture strength of the panel. It is beneficial or necessary that the fracture strength of the melt extruded or injection molded or hot pressed inorganic storage phosphor panel panels is as small as possible, while being high enough to sustain routine handling during use.

Thus, it is useful to compare grinding or tearing parameters for inventive and conventional inorganic storage phosphor panels. For practical purposes, it is useful to compare the peak torque required (e.g., used) to tear inorganic storage phosphor panels, using a standard or conventional method and equipment, such as the SER (Sentmanat Extension Rheometer) Universal Testing Platform from Xpansion Instruments (see www.xinst.com). One of the modes of operation of the instrument is the "high rate fracture testing", which is described in the website (see www.xinst.com). The operational details of the instrument are described in the SER 2004 Antec.pdf document found at www.xinst.com.

The fracture of the films measured by this device is defined by the following equation.

$$FS = T_p / 2Rt$$

Where FS—Fracture strength of the film being measured (Newtons/meter), Tp—the peak torque applied by the instrument (Newtons meter), R—radius of the drum (meters), and t—thickness of the film (meters)

The peak torque (Tp) required for tearing the panel is described the following equation $$Tp = FS \times 2 \times R \times t$$

The image quality assessments were done as described below. The x-ray source was a Carestream Health CS2200 x-ray generator and the images were scanned using a Carestream Health CS7600 intra oral dental scanner, in the super high resolution mode. The screens were subjected to an x-ray exposure of 70 kV, 7 mA, 0.16 sec. The pixel values were obtained using a flat field exposure of the storage phosphor screen and the resolution was obtained by imaging a line pair phantom, and visual observation. Image quality assessments obtained herein provide a measureable line pairs per mm (LP/mm) resolution consistently or across a set or batch of manufactured panels (e.g., an average resolution). For a constant x-ray exposure, fixed scanner conditions, the linearized pixel code value (cv) represents the speed of the storage phosphor screen in converting the incident x-ray photons to optical photons by photostimulated luminescence, which is detected by the detector and converted into digital signals.

Comparative Example 11

A solvent coated intraoral computed radiography panels (CS7600) was used as a comparative example 11. The panel consists of a BaFBrI phosphor coated on 7 mil PET support, and has a ~6 micron PVDF/PMMA overcoat, and the edges are sealed using the same overcoat material. The total thickness was 325 microns. Solvent coated intraoral computed radiography panels currently use a PET support. Applicants further were unable to tear an isolated 6 mil PET support, which could be used as the support for an intraoral computed radiography panel.

Inventive Example 9

Composite Thermoplastic Particle Production

Inorganic storage phosphor/thermoplastic composite pellets according to the present disclosure were prepared comprising 86% wt. barium flurobromoiodide (BFBrI) and 14% wt low density polyethylene (LDPE EM811A, available from Westlake Longview Corp. of Houston, Tex.), contained copper phthalocyanine, a blue dye, at a level of approximately 200 ppm with respect to the phosphor.

The formulation involved blending and compounding of the EM811A polymer resin with the BFBrI powder using a Leistritz GL-400 twin screw compounder. The screw speed was set at 300 RPM. The die temperature was set to 220° C. and 10 heating zones within the compounder were set to the temperatures shown in Table 19 below:

TABLE 19

| | | | | Zone | | | | | |
|---|---|---|---|---|---|---|---|---|---|
| 1 | 2 | 3 | 4 | 5 | 6 | 7 | 8 | 9 | 10 |

| Temp (° C.) | 220 | 220 | 220 | 220 | 220 | 220 | 220 | 220 | 220 | 220 |

After exiting the die, the inorganic storage phosphor/thermoplastic composite pellets, comprising LDPE loaded with BFBrI, entered a 25° C. water bath to cool and hardened into continuous strands. The strands were then fed into a pelletizer and dried at 40° C.

Extrusion of Inorganic Storage Phosphor Layer

The pelletized composite thermoplastic materials were loaded into a single screw Davis Standard extruder. Within the extruder, heating zones were set to the temperatures shown in Table 20.

TABLE 20

Davis Standard Extruder

| Zone | Temp |
|---|---|
| 1 | 390° F. |
| 2 | 420° F. |
| 3 | 430° F. |
| 4 | 430° F. |
| Gate | 430° F. |
| Die | 430° F. |

The pelletized material (composite thermoplastic) was extruded through a single die with the die temperature set at 430° F. form an extruded inorganic storage phosphor panel in the thickness range of 100-200 microns. The total thickness was 150 microns.

Inventive Example 10

Composite Thermoplastic Particle Production

A sample was prepared as described in inventive example 9, with a primary difference being that the pelletized material (composite thermoplastic) was coextruded through a two slot die with a carbon black containing low density polyethylene (LDPE EM811A, available from Westlake Longview Corp. of Houston, Tex.), with the die temperature set at 430° F., to form a bilayer extruded inorganic storage phosphor panel in the thickness range of 100-200 microns, with a carbon black containing LDPE layer. The blue dye concentration in the phosphor layer was 100 ppm with respect to the phosphor, and the total thickness was 325 microns.

ANALYSIS 4

| Sample | Support Thickness (microns) | Phosphor layer Thickness (microns) | Screen x-ray absorbance | Screen speed (linearized pixel CV) | (speed/ x-ray absorbance) | Screen resolution (LP/mm) | Peak torque (Tp) in Newton meter |
|---|---|---|---|---|---|---|---|
| Comparative Example 11 | 175 | 150 | 0.259 | 3556 | $1.37 \times 10^4$ | 17 | Could not be torn (maximum torque that can applied by the instrument is 0.2) |
| Inventive Example 9 | none | 150 | 0.203 | 2989 | $1.47 \times 10^4$ | 18 | 0.048 |
| Inventive Example 10 | 175 | 150 | 0.232 | 3186 | $1.37 \times 10^4$ | 18 | 0.102 |

Assessment

An important characteristic of the melt extruded or injection molded or hot pressed inorganic storage phosphor panel, is that it has a lower barium leaching rate than traditional solvent coated storage phosphor panels. The barium leaching rate from the panels was examined by submerging 0.67 gms of the panel in an extraction fluid, consisting of 1 gms of an aqueous solution of dilute nitric acid that was maintained at a pH of 2.8, at 25° C., for 72 hrs, and the concentration of barium ions in the solution was measured by ICP/MS.

Comparative Example 12

A solvent coated intraoral computed radiography panels (CS7600) was used as a comparative example 12. The panel consists of a BaFBrI phosphor coated on 7 mil PET support, and has a ~6 micron PVDF/PMMA overcoat, and the edges are sealed using the same overcoat material. The total surface area of the two major surfaces of the panel in contact with the extraction fluid was 25.42 cm$^2$, while the total surface are of the four edges (covered by the edge seal) of the panel in contact with the extraction fluid was 0.216 cm$^2$.

Comparative Example 13

A solvent coated intra oral computed radiography panels (CS7600) with the same construction as the one used in comparative example 12 was used, with the difference that the panel was chopped into three pieces. The total surface area of the two major surfaces of the panel in contact with the extraction fluid was 25.42 cm$^2$, while the total surface are of the twelve edges of the panel (some covered by the edge seal and some not covered by the edge seal) in contact with the extraction fluid was 0.402 cm$^2$. However, only four of the twelve edges are not covered by the edge seal. Hence, the surface area of the exposed (without edge seal) edges is 0.186 cm$^2$.

Inventive Example 11

Composite Thermoplastic Particle Production

Inorganic storage phosphor/thermoplastic composite pellets according to the present disclosure were prepared comprising 86% wt. barium flurobromoiodide (BFBrI) and 14% wt low density polyethylene (LDPE EM811A, available from Westlake Longview Corp. of Houston, Tex.), contained copper phthalocyanine, a blue dye, at a level of approximately 90 ppm with respect to the phosphor.

The formulation involved blending and compounding of the EM811A polymer resin with the BFBrI powder using a Leistritz GL-400 twin screw compounder. The screw speed was set at 300 RPM. The die temperature was set to 220° C. and 10 heating zones within the compounder were set to the temperatures shown in Table 21 below:

TABLE 21

| | Zone | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the inorganic storage phosphor/thermoplastic composite pellets, comprising LDPE loaded with BFBrI, entered a 25° C. water bath to cool and hardened into continuous strands. The strands were then fed into a pelletizer and dried at 40° C.

Extrusion of Inorganic Storage Phosphor Layer

The pelletized composite thermoplastic materials were loaded into a single screw Killion extruder. Within the extruder, heating zones were set to the temperatures shown in Table 22:

TABLE 22

| Killion Extruder | |
|---|---|
| Zone | Temp |
| 1 | 390° F. |
| 2 | 420° F. |
| 3 | 430° F. |
| 4 | 430° F. |
| Gate | 430° F. |
| Die | 430° F. |

The pelletized material (composite thermoplastic) was extruded through a single die with the die temperature set at 430° F. form an extruded inorganic storage phosphor panel in the thickness range of 100-200 microns. The total surface area of the two major surfaces of the panel in contact with the extraction fluid was 25.42 cm$^2$, while the total surface are of the four exposed edges of the panel in contact with the extraction fluid was 0.216 cm$^2$.

Inventive Example 12

An extruded inorganic storage phosphor panel with the same construction as the one used in inventive example 11 was used, with the difference that the panel was chopped into three pieces. The total surface area of the two major surfaces of the panel in contact with the extraction fluid was 25.42 cm$^2$, while the total surface are of the twelve exposed edges of the panel in contact with the extraction fluid was 0.402 cm$^2$.

| Sample | Concentration of barium ions in the extraction fluid after 72 hrs (ppm) | Concentration of barium ions in the extraction fluid after 72 hrs without the contribution from the major surface (ppm) | Rate of barium ions leaching into the extraction fluid without the contribution from the major surface (ppm/hr) | Rate of barium ions leaching into the extraction fluid per unit exposed edge area (ppm/hr/cm$^2$) |
|---|---|---|---|---|
| Comparative Example 12 | 320 | 2880 | 40 | 215 |
| Comparative Example 13 | 3200 | | | |
| Inventive Example 11 | 2200 | 1500 | 21 | 52 |
| Inventive Example 12 | 3700 | | | |

Assessment

An important characteristic of the melt extruded or injection molded or hot pressed inorganic storage phosphor panel is that it can be recycled. Certain embodiments of melt extruded or injection molded or hot pressed inorganic storage phosphor panels according to the application can be recycled and reused by simply grinding or crushing (e.g., reduce/break into small pieces) the inorganic storage phosphor panels using a standard device such as a grinder, cryo-grinder, densifiers, agglomerators, electromechanical grinder, mechanical crusher or any other suitable device, and the ground material can be melt extruded or injection molded or hot pressed again to form a recycled inorganic storage phosphor panel. Alternatively, in one recycling embodiment, after grinding or crushing the inorganic storage phosphor panels, the resulting material can be melt compounded to form composite thermoplastic particles, which are then compounded (e.g., melt extruded or injection molded or hot pressed) to form a recycled inorganic storage phosphor layer/panel. In order to be able to recycle inorganic storage phosphor panels effectively, it is beneficial or necessary that the recycled material/radiographic panels have an imaging performance that is comparable to that of the panels prior to recycling. Further, to be able to recycle inorganic storage phosphor panels effectively, it is beneficial or necessary that no individual components (e.g., blue dye, polymer, phosphor) chemically interact and/or degrade during recycling to form recycled inorganic storage phosphor panels. In addition, to be able to recycle inorganic storage phosphor panels effectively, it is beneficial or necessary that recycling process embodiments are mechanical and temperature compatible (e.g., does not degrade individual components) when compounding or forming recycled inorganic storage phosphor panels. Also, to be able to recycle inorganic storage phosphor panels effectively, it is beneficial or necessary that recycling process embodiments do not interfere or degrade subsequent radiographic imaging processes.

In some embodiments, a support can be attached to the inorganic storage phosphor layer and recycled, where the support is made of a polymer (e.g., thermoplastic polymer, a thermoplastic polyolefin polymer a thermoplastic polyolefin polymer that is a polyethylene) and the copper phthalocyanine based blue dye. In such embodiments, additional inorganic storage phosphor material can be added as desired during the re-cycling process (compounding and/or extrusion) to account for the added material being recycled from the support.

In one embodiment, a free standing inorganic storage phosphor panel with or without a support can include an inorganic storage phosphor layer of at least one polymer, an inorganic storage phosphor material, and a copper phthalocyanine based blue dye, that can be recycled one or more times by grinding the panel and extrusion (e.g., with optional compounding). In another embodiment, inorganic storage phosphor panels with or without a support can be re-cycled by melting (without grinding) followed by compounding to form a recycled manufactured panel. In yet another embodiment, an extrusion step forms sheets of inorganic storage phosphor layers that are larger than individual panels and the extruded sheet is cut (e.g., separated, sliced) into smaller or individual sized inorganic storage phosphor panels.

Existing storage phosphor panels are hard to recycle because existing storage phosphor panels are multilayered structures including, for example, of polyester (PET) support, with a phosphor/elastic polymer composite layer coating, and another polymer overcoat, and another polymer edge seal around the panel. Accordingly, recycling existing storage phosphor panels would require careful separation of each one of the components, without intermixing, and/or using complex solvents and new and inventive processes.

Image Quality Assessment

The image quality assessments were done as described below. The x-ray source was a Carestream Health CS2200 x-ray generator and the images were scanned using a Carestream Health CS7600 intra oral dental scanner, in the super high resolution mode. The pixel values were obtained using a flat field exposure of the storage phosphor screen and the resolution was obtained by imaging a line pair phantom, and visual observation. Image quality assessments obtained herein provide a measureable line pairs per mm (LP/mm) resolution consistently or across a set or batch of manufactured panels (e.g., an average resolution). For a constant x-ray exposure, fixed scanner conditions, the linearized pixel code value (cv) represents the speed of the storage phosphor screen in converting the incident x-ray photons to optical photons by photostimulated luminescence, which is detected by the detector and converted into digital signals.

The x-ray generator was set to an exposure level of 70 kV, 7 mA, 0.16 sec. with a 3.5 mm Al filter. The x-ray transmittance was measured using a Raysafe Xi Unfors densitometer (set at the "hi" level), with and without the sample, and the absorbance is calculated using Beer's law (Absorbance=log(Transmittance through air/Transmittance through screen).

Comparative Example 14

Composite Thermoplastic Particle Production

Inorganic storage phosphor/thermoplastic composite pellets according to the present disclosure were prepared comprising 86% wt. barium flurobromoiodide (BFBrI) and 14% wt low density polyethylene (LDPE EM811A, available from Westlake Longview Corp. of Houston, Tex.), contained copper phthalocyanine, a blue dye, at a level of approximately 60 ppm with respect to the phosphor.

The formulation involved blending and compounding of the EM811A polymer resin with the BFBrI powder using a Leistritz GL-400 twin screw compounder. The screw speed was set at 300 RPM. The die temperature was set to 220° C. and 10 heating zones within the compounder were set to the temperatures shown in Table 23 below:

TABLE 23

| | Zone | | | | | | | | | |
|---|---|---|---|---|---|---|---|---|---|---|
| | 1 | 2 | 3 | 4 | 5 | 6 | 7 | 8 | 9 | 10 |
| Temp (° C.) | 220 | 220 | 220 | 220 | 220 | 220 | 220 | 220 | 220 | 220 |

After exiting the die, the inorganic storage phosphor/thermoplastic composite pellets, comprising LDPE loaded with BFBrI, entered a 25° C. water bath to cool and hardened into continuous strands. The strands were then fed into a pelletizer and dried at 40° C.

Extrusion of Inorganic Storage Phosphor Layer

The pelletized composite thermoplastic materials were loaded into a single screw Davis Standard extruder. Within the extruder, heating zones were set to the temperatures shown in Table 24

TABLE 24

| Davis Standard Extruder | |
|---|---|
| Zone | Temp |
| 1 | 390° F. |
| 2 | 420° F. |
| 3 | 430° F. |
| 4 | 430° F. |
| Gate | 430° F. |
| Die | 430° F. |

The pelletized material (composite thermoplastic) was extruded through a single die with the die temperature set at 430° F. form an extruded inorganic storage phosphor panel in the thickness range of 100-200 microns.

Inventive Example 13

The panels generated from comparative example 14 were ground using a food processor (Hamilton Beach Big Mouth Deluxe 14-Cup Food Processor)—put the panels into food processor, run on high speed for about 4 minutes or until ground into small pieces, and the powdered flakes from the food processor were compounded and extruded according the procedure described in comparative example 14. In inventive example 13, a ratio of the speed to the x-ray absorbance of the recycled panel was within 15% of the panel prior to recycling.

ANALYSIS 6

| Sample | X-ray absorbance | Screen speed (linearized pixel CV) | Screen speed normalized to x-ray absorbance | Screen resolution (LP/mm) |
|---|---|---|---|---|
| Comparative Example 14 | 0.251 | 3339 | $1.33 \times 10^4$ | 17 |
| Inventive Example 13 | 0.246 | 3176 | $1.29 \times 10^4$ | 18 |

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

Certain exemplary method and/or apparatus embodiments according to the application can provide improved re-cycled inorganic storage phosphor layers/panels. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. A re-cycled inorganic storage phosphor panel comprising,
   an inorganic storage phosphor layer comprising at least one polymer, an inorganic storage phosphor material, and a copper phthalocyanine based blue dye; and
   a support attached to the inorganic storage phosphor layer.

2. A method for recycling an inorganic storage phosphor panel comprising:
   providing an inorganic storage phosphor panel comprising at least one polymer, an inorganic storage phosphor material, and a copper phthalocyanine based blue dye;
   mechanically grinding the inorganic storage phosphor panel into a powder or flakes; and
   melt extruding, injection molding or hot pressing the ground powder or flakes to form a recycled manufactured inorganic storage phosphor panel.

3. The method of claim 2, further comprising:
   compounding the ground powder or flakes into pellets; and
   melt extruding, injection molding or hot pressing the compounded pellets to form the recycled manufactured inorganic storage phosphor panel.

4. The method of claim 2, further comprising:
   exposing the recycled manufactured inorganic storage phosphor layer to x-rays to form a latent image; and
   exposing the latent image in the recycled manufactured inorganic storage phosphor layer to excitation light to generate a digital image of the latent image,
   where a ratio of the speed to the x-ray absorbance of the panel is within 10% of the panel prior to recycling.

5. The method of claim 4, where the latent image is a flat field image.

* * * * *